(12) United States Patent
Gray

(10) Patent No.: US 6,649,800 B1
(45) Date of Patent: Nov. 18, 2003

(54) PROCESS FOR THE PREPARATION OF POLYALKYLPHENOXYAMINOALKANES

(75) Inventor: James A. Gray, Novato, CA (US)

(73) Assignee: Chevron Oronite Company LLC, San Ramon, CA (US)

(*) Notice: Subject to any disclaimer, the term of this patent is extended or adjusted under 35 U.S.C. 154(b) by 0 days.

(21) Appl. No.: 10/285,755

(22) Filed: Oct. 31, 2002

(51) Int. Cl.$^7$ .................... C07C 209/62; C07C 209/16
(52) U.S. Cl. .................. 564/413; 564/353; 564/354
(58) Field of Search ............................ 564/353, 354, 564/413

(56) References Cited

U.S. PATENT DOCUMENTS

| | | | |
|---|---|---|---|
| 4,381,401 A | 4/1983 | Poindexter | 556/410 |
| 5,669,939 A | 9/1997 | Cherpeck | 44/425 |
| 5,851,242 A | 12/1998 | Cherpeck et al. | 44/425 |
| 6,384,280 B1 | 5/2002 | Cherpeck | 564/353 |
| 6,486,352 B1 * | 11/2002 | Gray | 564/353 |

FOREIGN PATENT DOCUMENTS

| | | |
|---|---|---|
| DE | 19711004 A1 | 10/1997 |
| JP | 2592732 B2 | 3/1997 |

OTHER PUBLICATIONS

U.S. patent application Ser. No. 10/185,469, Gray, filed Jun. 28, 2002.
Martin E. Dyen and Daniel Swern, *Chemistry Reviews* (1967), pp. 197–246.

* cited by examiner

*Primary Examiner*—Brian Davis
(74) *Attorney, Agent, or Firm*—S. G. K. Lee

(57) ABSTRACT

An improved process for the preparation of polyalkylphenoxyaminoalkanes which comprises the aminoethylation of a polyalkylphenol compound in the presence of a basic catalyst with 2-oxazolidinone or a derivative thereof having the following formula:

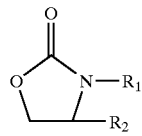

wherein $R_1$ and $R_2$ are independently hydrogen or lower alkyl having 1 to about 6 carbon atoms and wherein the polyalkyl group of said polyalkylphenol has an average molecular weight in the range of about 600 to 5,000 and wherein the process is carried out in the presence of an alcohol.

29 Claims, No Drawings

PROCESS FOR THE PREPARATION OF POLYALKYLPHENOXYAMINOALKANES

FIELD OF THE INVENTION

The present invention relates to an improved process for the preparation of polyalkylphenoxyaminoalkanes. More particularly, this invention relates to a process for the preparation of polyalkylphenoxyaminoalkanes which comprises the aminoethylation of a polyalkylphenol compound with 2-oxazolidinone or a derivative thereof in the presence of an alcohol.

BACKGROUND OF THE INVENTION

Polyalkylphenoxyaminoalkanes are known fuel additives useful in the prevention and control of engine deposits. U.S. Pat. Nos. 5,669,939 and 5,851,242 describes a process for preparing these compounds. The process involves initially hydroxylating a polyalkylphenol with an alkylene carbonate in the presence of a catalytic amount of an alkali metal hydride or hydroxide, or alkali metal salt, to provide a polyalkylphenoxyalkanol which is subsequently reacted with an appropriate amine to provide the desired polyalkylphenoxyaminoalkane.

2-oxazolidinones or derivatives thereof are well described. For example, Martin E. Dyen and Daniel Swern, *Chemistry Reviews* (1967), pages 197–246 describes 2-oxazolidinones in detail. The use of 2-oxazolidinones or derivatives thereof in the aminoethylation of phenols is well known in the art.

U.S. Pat. No. 4,381,401 discloses the reaction of 2-oxazolidinone or N-substituted derivatives thereof with aromatic amine hydrochlorides at elevated temperatures to produce 1,2-ethanediamines. The 1,2-ethanediamines produced are an important class of materials which are useful as intermediates for the production of pharmaceuticals, photographic chemicals and other compositions.

Japanese Patent Publication No. JP 2592732 B2 discloses a method of producing phenoxyethylamines by reacting, under base conditions, low molecular weight phenols and 2-oxazolidinone. Phenoxyethylamines are important raw materials for pharmaceuticals and pesticides.

German Patent Publication DE 19711004 A1 discloses the use of 2-oxazolidinone to prepare phenoxyaminoalkanes from low molecular weight phenols. 24-(Phenoxyphenoxy) ethylamine and ethyl 2-(phenoxyphenoxy)ethylcarbamate are sequentially prepared in high yield and selectivity by the aminoethylation of 4-phenoxyphenol with 2-oxazolidinone under inert atomsphere, followed by amidation of 2-4-(phenoxyphenoxy)ethylamine with carbonate derivatives.

U.S. Pat. No. 6,384,280 teaches the use of 2-oxazolidinone or a derivative thereof in aminoethylation transformations involving high molecular weight polyalkylphenols to provide polyalkylphenoxyaminoalkanes of the type disclosed in U.S. Pat. Nos. 5,669,939 and 5,851,242.

Commonly assigned copending U.S. patent application Ser. No. 10/185,469, filed Jun. 28, 2002, a process for the preparation of polyalkylphenoxyaminoalkanes comprising the aminoethylation of a polyalkylphenol compound with β-amino alcohol and dialkyl carbonate, which process may contain an optional alcohol.

SUMMARY OF THE INVENTION

The present invention provides an improved process for the preparation of polyalkylphenoxyaminoalkanes which comprises the aminoethylation of a polyalkylphenol compound in the presence of a basic catalyst with 2-oxazolidinone or a derivative thereof having the following formula:

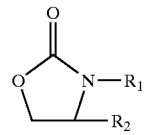

wherein $R_1$ and $R_2$ are independently hydrogen or lower alkyl having 1 to about 6 carbon atoms and wherein the polyalkyl group of the polyalkylphenol has an average molecular weight in the range of about 600 to 5,000 and wherein the process is carried out in the presence of an alcohol.

The alcohol has the structure $R_3$—OH wherein $R_3$ is an alkyl group having about 3 to 7 carbon atoms. The molar ratio of the alcohol to the polyalkylphenol compound is normally in the range of about 0.2:1 to 5:1.

The aminoethylation reaction of the present invention readily occurs using a basic catalyst selected from the group consisting of alkali metal lower alkoxides, alkali hydrides or alkali metal hydroxides in the temperature range of about 100° C. to 250° C., wherein the molar ratio of 2-oxazolidinone or a derivative thereof to polyalkylphenol compound is about 5:1 to 0.9:1 and wherein the number of equivalents of basic catalyst per equivalent of polyalkylphenol is about 0.05:1 to 1:1.

Among other things, the present invention relates to an improved process for the preparation of polyalkylphenoxyaminoalkanes in the presence of an alcohol that provides increased polyisobutylphenol conversion and reduced thermal degradation of 2-oxazolidinone in the process. Moreover, the use of an alcohol was found to mitigate the negative effect of sediment in unfiltered polyisobutylphenol (still contains salts from the neutralized alkylation catalyst) on product color. The use of polyisobutylphenol containing alkylation catalyst sediment is preferred over filtered or washed polyisobutylphenol due to process economics.

DETAILED DESCRIPTION OF THE INVENTION

As noted above, the present invention provides an improved process for the preparation of polyalkylphenoxyaminoalkanes which comprises an aminoethylation of a polyalkylphenol compound in the presence of a basic catalyst with 2-oxazolidinone or a derivative thereof having the following formula:

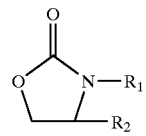

wherein $R_1$ and $R_2$ are independently hydrogen or lower alkyl having 1 to about 6 carbon atoms and wherein the polyalkyl group of the polyalkylphenol has an average molecular weight in the range of about 600 to 5,000 and wherein the process is carried out in the presence of an alcohol.

The reaction may be illustrated by the following:

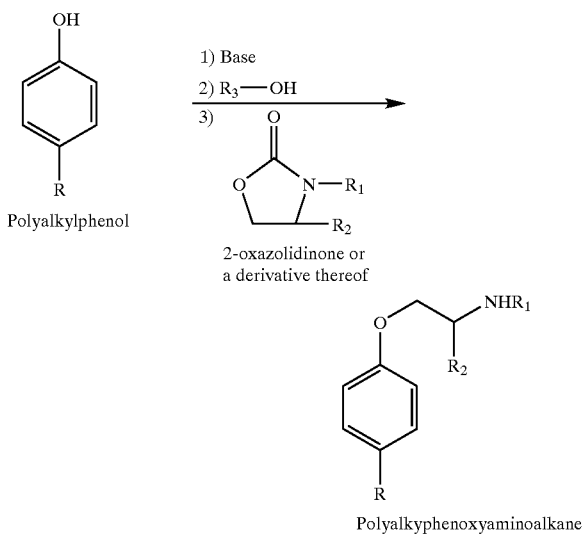

Polyalkyphenoxyaminoalkane wherein R is a polyalkyl group having a molecular weight in the range of about 600 to 5,000, and $R_1$, $R_2$ and $R_3$ are as herein described.

Definitions

Prior to discussing the present invention in detail, the following terms will have the following meanings unless expressly stated to the contrary.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "polyalkyl" refers to an alkyl group which is generally derived from polyolefins which are polymers or copolymers of mono-olefins, particularly 1-mono-olefins, such as ethylene, propylene, butylene, and the like. Preferably, the mono-olefin employed will have about 2 to 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

Polyalkylphenoxyaminoalkanes may be prepared by the process of the present invention which comprises an aminoethylation of a polyalkylphenol compound with 2-oxazolidinone or a derivative thereof having the following formula:

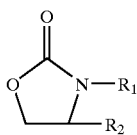

wherein $R_1$ and $R_2$ are defined herein, in the presence of a catalytic amount of an alkali metal lower alkoxide, alkali hydride or alkali metal hydroxide.

Polyalkylphenols are well known materials and are typically prepared by the alkylation of phenol with the desired polyolefin or chlorinated polyolefin. A further discussion of polyalkylphenols can be found, for example, in U.S. Pat. Nos. 4,744,921 and 5,300,701.

Accordingly, polyalkylphenols may be prepared from the corresponding olefins by conventional procedures. For example, polyalkylphenols may be prepared by reacting the appropriate olefin or olefin mixture with phenol in the presence of an alkylating catalyst at a temperature of from about 25° C. to 150° C., and preferably about 30° C. to 100° C. either neat or in an essentially inert solvent at atmospheric pressure. A preferred alkylating catalyst is boron trifluoride. Molar ratios of reactants may be used. Alternatively, molar excesses of phenol can be employed, i.e., about 2 to 3 equivalents of phenol for each equivalent of olefin with unreacted phenol recycled. The latter process maximizes monoalkylphenol.

Examples of inert solvents include heptane, benzene, toluene, chlorobenzene and 250 thinner which is a mixture of aromatics, paraffins and naphthenes. Kerosene-type jet fuel is another example of the latter mixture. Other examples of inert solvents that are aromatic mixtures include Exxon Aromatic 100, Exxon Aromatic 150, Solvesso 100, Total Solvarex 9 and the like.

The polyalkyl group on the polyalkylphenols employed in the invention is generally derived from polyolefins which are polymers or copolymers of mono-olefins, particularly 1-mono-olefins, such as ethylene, propylene, butylene, and the like. Preferably, the mono-olefin employed will have about 2 to 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkylphenols are polyisobutenes which comprise at least about 20% of the more reactive methylvinylidene isomer, preferably at least about 50% and more preferably at least about 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain. Examples of suitable polyisobutenes having a high alkylvinylidene content include Ultravis 30, a polyisobutene having a number average molecular weight of about 1,300 and a methylvinylidene content of about 74%, and Ultravis 10, a polyisobutene having a number average molecular weight of about 950 and a methylvinylidene content of about 76%, both formerly manufactured by British Petroleum. Similar polyisobutenes are currently available from BASF, ChevronTexaco, and Texas Petrochemicals.

Typically, the polyalkyl group on the polyalkylphenol has a molecular weight in the range of about 600 to 5,000, preferably about 600 to 3,000, more preferably about 700 to 3,000, and most preferably about 900 to 2,500. The polyalkyl group on the polyalkylphenol may be in any position in the phenol ring. However, substitution at the para position is preferred.

As noted above, the polyalkylphenol compound is reacted with 2-oxazolidinone or a derivative thereof having the formula illustrated herein above, wherein $R_1$ and $R_2$ are independently hydrogen or lower alkyl having 1 to about 6 carbon atoms. Preferably, one of $R_1$ and $R_2$ is hydrogen or lower alkyl of 1 to about 4 carbon atoms, and the other is hydrogen. More preferably, one of $R_1$ and $R_2$ is hydrogen, methyl, or ethyl, and the other is hydrogen. Still more preferably, $R_1$ is hydrogen, methyl, or ethyl, and $R_2$ is hydrogen. Most preferably, both $R_1$ and $R_2$ are hydrogen. Examples of such compounds include, but are not limited to, 2-oxazolidinone, 3-methyl-2-oxazolidinone, 4-methyl-2-oxazolidinone, and 3-ethyl-2-oxazolidinone. The 2-oxazolidinone compound is preferred. These compounds are readily commercially available. For instance, 2-oxazolidinone and 3-methyl-2-oxazolidinone may be purchased from Aldrich Chemical Company. Alternatively, these compounds may be synthesized by conventional methods apparent to the skilled artisan.

The basic catalyst employed in the process of the present invention will generally be any of the well known basic catalyst selected from the group of alkali metal lower alkoxides, alkali hydrides or alkali metal hydroxides. Typical alkali metal lower alkoxides include, but are not limited to, sodium methoxide, potassium methoxide, sodium ethoxide, potassium ethoxide, sodium propoxide, potassium propoxide, sodium isopropoxide, potassium isopropoxide, sodium butoxide, potassium butoxide. Typically, the alkali metal lower alkoxides will contain 1 to about 6, preferably 1 to about 4, carbon atoms. Preferably, the alkali metal lower alkoxide is sodium methoxide. Sodium hydride and potassium hydride are typical alkali hydrides. Examples of alkali metal hydroxides include, but are not limited to, sodium hydroxide, lithium hydroxide, or potassium hydroxide. Sodium hydroxide and potassium hydroxide are preferred.

Typically, the reaction temperature for the aminoethylation reaction will be in the range of about 100° C. to 250° C., and preferably in the range of about 130° C. to 210° C. The reaction pressure will generally be atmospheric or lower. Lower pressures may be used to facilitate the removal of carbon dioxide. Other carbon dioxide scavengers may be employed to facilitate the reaction, such as, for example, magnesium oxide or calcium oxide.

When lower alcohols are used, it is advantageous to carry out the reaction under pressure, for example up to 100 psig depending on the alcohol, in order to raise the boiling temperature of the reaction mixture to the optimal level for the reaction. In this case, some means must be provided to remove $CO_2$ so that carbonate salts are not formed in the reactor. This may be accomplished by controlled boiling of the reaction mixture so that solvent vapors carry the $CO_2$ overhead into a column that condenses and recycles the solvent while venting the $CO_2$. Nitrogen sparging into the reaction mixture or purging of the reactor head space may also be used to accomplish the same end while maintaining pressure on the reactor.

The molar ratio of 2-oxazolidinone or a derivative thereof to the polyalkylphenol compound is normally in the range of about 5:1 to 0.9:1, and preferably will be in the range of about 2:1 to 1:1. In general, the number of equivalents of the basic catalyst per equivalents of polyalkylphenol will be in the range of about 0.05:1 to 1:1, and preferably in the range of about 0.1:1 to 1:1.

The aminoethylation reaction may be carried out neat or in the presence of a solvent which is inert to the reaction of the polyalkylphenol compound and the 2-oxazolidinone or a derivative thereof. An inert solvent is often used to facilitate handling of the polyalkylphenol and to promote good contacting of the reactants. When employed, examples of inert solvents include heptane, benzene, toluene, chlorobenzene and 250 thinner which is a mixture of aromatics, paraffins and naphthenes. Kerosene-type jet fuel is another example of the latter mixture. Other examples of inert solvents that are aromatic mixtures include Exxon Aromatic 100, Exxon Aromatic 150, Solvesso 100, Total Solvarex 9 and the like. Other solvents apparent to those skilled in the art may also be used. For example, any number of ethers, aprotic polar solvents or alcohols may also be useful in the process of the present invention.

In accordance with the present invention, an alcohol is employed in the aminoethylation process. The alcohol has the structure $R_3$—OH wherein $R_3$ is an alkyl group having about 3 to 7 carbon atoms, preferably about 5 to 7 carbon atoms, most preferably about 6 carbon atoms. Examples of typical alcohols include n-propanol, n-butanol, 1-pentanol, 1-hexanol, 1-heptanol, and mixed isomers of each of the foregoing alcohols including branched- or straight-chain alcohols. 1-Hexanol or hexanol isomers are preferred. Examples of commercial alcohols available from Exxon-Mobil Chemical that are a mix of several isomers include Exxal 6 (hexyl alcohol) and Exxal 7 (isoheptyl alcohol).

The molar ratio of the alcohol to the polyalkylphenol compound is normally in the range of about 0.2:1 to 5:1, preferably about 0.4:1 to 2:1, and most preferably about 0.5:1 to 1.5:1.

The aminoethylation reaction will generally be carried out over a period of about 2 to 24 hours, and preferably over a period of about 3 to 20 hours. Upon completion of the reaction, the desired polyalkyphenoxyaminoalkane is isolated using conventional techniques.

EXAMPLES

The invention will be further illustrated by the following examples, which set forth particularly advantageous process embodiments. While the Examples are provided to illustrate the present invention, they are not intended to limit it. This application is intended to cover those various changes and substitutions that may be made by those skilled in the art without departing from the spirit and scope of the appended claims.

Example 1

Improvement Using 1-Hexanol

Preparation of Solution Containing

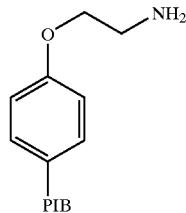

PIB
(avg. molecular weight ~950)

Potassium hydroxide (assay 85%, 17.3 grams) and a solution of 4-polyisobutyl phenol wherein the polyisobutyl group has an average molecular weight of about 950 (2521.3 grams, prepared as in Example 1 of U.S. Pat. No. 5,300,701 except it was not filtered or washed to remove the salts from the neutralized alkylation catalyst) were added to a 4-L reaction flask equipped with a magnetic stirrer, Dean-Stark trap, reflux condenser, nitrogen inlet and temperature controller. The solution of 4-polyisobutyl phenol contained about 32.7% Solvesso 100 aromatic solvent and had a hydroxyl number of 38.8 mg KOH/g. The solution also contained 5.3% unconverted polyisobutylene on a solvent-free basis. The reaction mixture was heated at about 130° C. under a pressure of about 150–160 mm Hg until no more water came overhead by azeotropic distillation with the aromatic solvent. The reactor contents were cooled under nitrogen, a 25.6-gram sample was removed and the remaining solution of dehydrated 4-polyisobutyl phenol (2410.5 grams) was transferred to jars and stored in a dry box until needed for the aminoethylation reaction.

Dehydrated 4-polyisobutyl phenol solution (400.0 grams) from above and 1-hexanol (29.2 grams, anhydrous from Aldrich), were added to a separate 1-L reactor equipped with a total reflux condenser and nitrogen purge. The reaction mixture was heated to about 150° C. at atmospheric pressure under nitrogen purge. After adding 2-oxazolidinone (25.1 grams, assay 99%, from Avocado Research Chemicals Ltd.) to the reactor at about 150° C., the temperature was increased until the mixture refluxed vigorously at about 176° C. while purging with nitrogen at atmospheric pressure. These reaction conditions were maintained for four hours.

The reactor was cooled to about 85° C. and a yielded 441.9 grams of crude product. After removing a sample, magnesium silicate (10.1 grams Magnesol HMR LS), filter aid (1.01 gram of Celite HyFlo Super Cel), and deionized water (2.21 grams) were added to the remaining 414.9 grams of crude product and the mixture stirred for one hour at about 85° C. The crude product mixture was filtered with a pressure filter and yielded 388.4 grams of amber colored filtrate and 27.3 grams of filter cake. Table 2 summarizes the properties of the filtrate.

After evaporating solvent from the filtrate in a vacuum oven at about 150° C., $^1$H NMR (CDCl$_3$) was used to quantify the conversion of 4-polyisobutyl phenol and the selectivity to aminoethylate. Unconverted 4-polyisobutyl gives a doublet at 6.73 ppm for two protons on the aromatic ring, while converted 4-polyisobutyl gives a doublet at 6.81 ppm for the same two protons. The aminoethylate was identified by 7.25 (ABq, 2H), 6.8 (ABq, 2H), 4.0 (t, 2H), 3.1 (t, 2H) as described in the examples of U.S. Pat. No. 6,384,280, and the mole percent aminoethylate was calculated based on the NMR data. The aminoethylate content was converted to a weight percent solvent-free sample basis by combining the NMR data (mole percent) with the percent residual polyisobutylene content and component molecular weights calculated from the hydroxyl number of the 4-polyisobutyl phenol.

The conversion of 4-polyisobutyl phenol was 85% compared to 71% in Comparative Example A while aminoethylate selectivity was essentially unchanged (Table 2). The aminoethylate content of the polymer was 72% compared to 62% in Comparative Example A. Table 2 shows that the color (ASTM D1500), basic nitrogen (ASTM D2896), and total nitrogen of the filtrate improved compared to Comparative Example A. The nitrogen content of the filtrate indicated that 2-oxazolidinone utilization improved as well. Thus, there is a clear benefit in using 1-hexanol.

Example 2

Improvement Using Mixed Isomer Hexanol

Preparation of Solution Containing

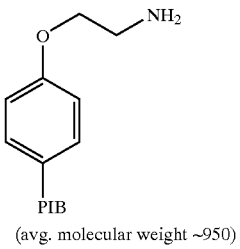

(avg. molecular weight ~950)

Dehydrated 4-polyisobutyl phenol solution like prepared in Example 1 (400.0 grams) and mixed isomer hexanol (29.3 grams, Exxal 6 from ExxonMobil Chemical Company, dried by distillation), were added to a separate 1-L reactor equipped with a total reflux condenser and nitrogen purge. The reaction mixture was heated to about 150° C. at atmospheric pressure under nitrogen purge. After adding 2-oxazolidinone (25.1 grams, assay 99%, from Avocado Research Chemicals Ltd.) to the reactor at about 150° C., the temperature was increased until the mixture refluxed vigorously at about 175° C. while purging with nitrogen at atmospheric pressure. These reaction conditions were maintained for four hours.

The reactor was cooled to about 85° C. and a yielded 440.9 grams of crude product. After removing a sample, magnesium silicate (11.7 grams Magnesol HMR LS), filter aid (1.17 grams of Celite HyFlo Super Cel), and deionized water (1.99 grams) were added to the remaining 415 grams of crude product and the mixture stirred for one hour at about 85° C. The crude product mixture was filtered with a pressure filter and yielded 386 grams of amber colored filtrate and 31.1 grams of filter cake. Table 2 summarizes the properties of the filtrate.

This example gives results very close to Example 1 and shows that a mixed-isomer hexanol (about 62% branched-chain and about 38% straight-chain isomers by GC) works just as well as 1-hexanol. This example also confirms the benefit to 4-polyisobutyl phenol conversion and filtrate color of employing a lower alcohol (less than eight carbon atoms).

Example 3

Improvement Using 1-Hexanol

Preparation of Solution Containing

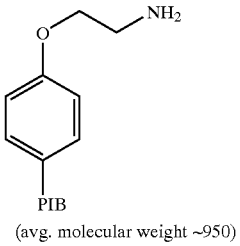

(avg. molecular weight ~950)

Potassium hydroxide (assay 85%, 12.3 grams) and a solution of 4-polyisobutyl phenol wherein the polyisobutyl group has an average molecular weight of about 950 (2523.4 grams, prepared as in Example 1 of U.S. Pat. No. 5,300,701) were added to a 4-L reaction flask equipped with a magnetic stirrer, Dean-Stark trap, reflux condenser, nitrogen inlet and temperature controller. The solution of 4-polyisobutyl phenol contained about 26.1% Total Solvarex 9 aromatic solvent and had a hydroxyl number of 41.4 mg KOH/g. There was no sediment from the neutralized alkylation catalyst in this solution. The solution also contained 4.8% unconverted polyisobutylene on a solvent-free basis. The reaction mixture was heated at about 130° C. under a pressure of about 130–140 mm Hg until no more water came overhead by azeotropic distillation with the aromatic solvent. The reactor contents were cooled under nitrogen, a 25-gram sample was removed and the remaining solution of dehydrated 4-polyisobutyl phenol (2410.5 grams) was transferred to jars and stored in a dry box until needed for the aminoethylation reaction.

Dehydrated 4-polyisobutyl phenol solution (400.0 grams) from above and 1-hexanol (31.2 grams, anhydrous from Aldrich), were added to a separate 1-L reactor equipped with a total reflux condenser and nitrogen purge. The reaction mixture was heated to about 150° C. at atmospheric pressure under nitrogen purge. After adding 2-oxazolidinone (26.8 grams, assay 99%, from Avocado Research Chemicals Ltd.) to the reactor at about 150° C., the temperature was increased until the mixture refluxed vigorously at about 177° C. while purging with nitrogen at atmospheric pressure. These reaction conditions were maintained for four hours.

The reactor was cooled to about 85° C. and a yielded 444.1 grams of crude product. After removing a sample, magnesium silicate (7.16 grams Magnesol HMR LS), filter aid (0.72 gram of Celite HyFlo Super Cel), and deionized water (2.22 grams) were added to the remaining 418.4 grams of crude product and the mixture stirred for one hour at about 85° C. The crude product mixture was filtered with a pressure filter and yielded 394.4 grams of amber colored filtrate and 21.8 grams of filter cake. Table 2 summarizes the properties of the filtrate.

The conversion of 4-polyisobutyl phenol was 81% compared to 76% in Comparative Example E while aminoethylate selectivity was 87% compared to 91% in Comparative Example E (Table 2). The aminoethylate content of the polymer was 68% compared to 66% in Comparative Example E. Table 2 shows that basic and total nitrogen content of the polymer improved compared to Comparative Example E as well as the 2-oxazolidinone utilization. This again shows there is a benefit in using 1-hexanol.

Comparative Example A

No Alcohol

Preparation of Solution Containing

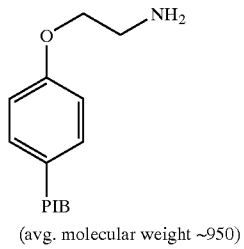

(avg. molecular weight ~950)

Dehydrated 4-polyisobutyl phenol solution (366.0 grams) from Example 1 and ExxonMobil Aromatic 100 Solvent (11.8 grams) were added to a separate 1-L reactor equipped with a total reflux condenser and nitrogen purge. The reaction mixture was heated to about 150° C. at atmospheric pressure under nitrogen purge. After adding 2-oxazolidinone (23.0 grams, assay 99%, from Avocado Research Chemicals Ltd.) to the reactor at about 150° C., the temperature was increased to about 180° C. Nitrogen purging was stopped and the pressure was lowered to about 700 mm Hg in order to cause a vigorous reflux. The temperature was held at about 180° C. for four hours and the pressure gradually lowered to about 656 mm Hg to maintain the refluxing. The reactor was cooled to about 85° C. and a yielded 388.7 grams of crude product. After removing a sample, magnesium silicate (9.2 grams Magnesol HMR LS), filter aid (0.91 grams of Celite HyFlo Super Cel), and deionized water (1.94 grams) were added to the remaining 362 grams of crude product and the mixture stirred for one hour at about 85° C. The crude product mixture was filtered with a pressure filter and yielded 335.7 grams of amber colored filtrate and 23.2 grams of filter cake. Table 2 summarizes the properties of the filtrate. The aminoethylate content of the polymer was 62%. The conversion of 4-polyisobutyl phenol was 71% and the selectivity to aminoethylate was 91% (Table 2).

The total nitrogen is higher than the basic nitrogen because the product contains some byproducts. These include acylated intermediate that has not yet rearranged to form the aminoethylate, a urea byproduct from further reaction of the aminoethylate, and possibly traces of other nitrogen-containing impurities.

The color was relatively dark at 5.5. The nitrogen content of the filtrate indicated that about 87% of the 2-oxazolidinone was utilized in the product.

Comparative Example B

Slight Improvement Using 1-Octanol

Preparation of Solution Containing

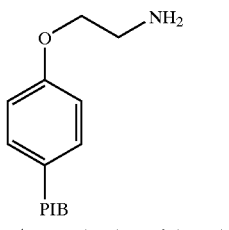

(avg. molecular weight ~950)

Dehydrated 4-polyisobutyl phenol solution like prepared in Example 1 (400.0 grams) and 1-octanol (37.2 grams, anhydrous from Aldrich), were added to a separate 1-L reactor equipped with a total reflux condenser and nitrogen purge. The reaction mixture was heated to about 150° C. at atmospheric pressure under nitrogen purge. After adding 2-oxazolidinone (25.1 grams, assay 99%, from Avocado Research Chemicals Ltd.) to the reactor at 150° C., the temperature was increased to about 180° C. Nitrogen purging was stopped and the pressure was lowered to about 650 mm Hg in order to cause a vigorous reflux. The temperature was held at about 180° C. for four hours and the pressure gradually lowered to about 636 mm Hg to maintain vigorous refluxing.

The reactor was cooled to about 85° C. and a yielded 450.2 grams of crude product. After removing a sample, magnesium silicate (11.7 grams Magnesol HMR LS), filter aid (1.17 grams of Celite HyFlo Super Cel), and deionized water (2.02 grams) were added to the remaining 424.7 grams of crude product and the mixture stirred for one hour at about 85° C. The crude product mixture was filtered with a pressure filter and yielded 394.9 grams of amber colored filtrate and 30.3 grams of filter cake. Table 2 summarizes the properties of the filtrate.

When compared to Comparative Example A, this example shows that 1-octanol gives some improvement in 4-polyisobutyl phenol conversion and aminoethylate content in the polymer, but does not result in a lighter filtrate color or a significant improvement in utilization of the nitrogen in the 2-oxazolidinone. This example shows that alcohol molecular weight is an important consideration. Preferred alcohols should have less than eight carbon atoms.

Comparative Example C

Slight Improvement Using 2-Ethylhexanol

Preparation of Solution Containing

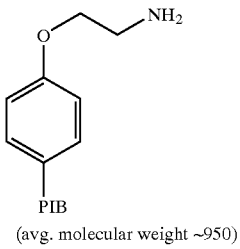

PIB
(avg. molecular weight ~950)

Dehydrated 4-polyisobutyl phenol solution from Example 1 (400.0 grams) and 2-ethyl-1-hexanol (37.2 grams, 99.8% assay from Aldrich), were added to a separate 1-L reactor equipped with a total reflux condenser and nitrogen purge. The reaction mixture was heated to about 150° C. at atmospheric pressure under nitrogen purge. After adding 2-oxazolidinone (25.1 grams, assay 99%, from Avocado Research Chemicals Ltd.) to the reactor at 150° C., the temperature was increased to about 180° C. Nitrogen purging was stopped and the pressure was lowered to about 730 mm Hg in order to cause reflux. The temperature was held at about 180° C. for four hours and the pressure gradually lowered to about 670 mm Hg to maintain vigorous refluxing.

The reactor was cooled to about 85° C. and a yielded 450.6 grams of crude product. After removing a sample, magnesium silicate (10.1 grams Magnesol HMR LS), filter aid (1.01 grams of Celite HyFlo Super Cel), and deionized water (2.25 grams) were added to the remaining 424 grams of crude product and the mixture stirred for one hour at about 85° C. The crude product mixture was filtered with a pressure filter and yielded 398.8 grams of amber colored filtrate and 26.1 grams of filter cake. Table 2 summarizes the properties of the filtrate.

This example gives results (Table 2) that are similar to Comparative Example B using 1-octanol. When compared to Comparative Example A, this example shows that 2-ethyl-1-hexanol gives some improvement in 4-polyisobutyl phenol conversion and aminoethylate content in the polymer, but does not result in a significantly lighter filtrate color or a significant improvement in utilization of the nitrogen in the 2-oxazolidinone. This example confirms that alcohol molecular weight is an important consideration and that branched and straight chain C8 alcohols give about the same effect.

Comparative Example D

No Improvement Using 1-Decanol

Preparation of Solution Containing

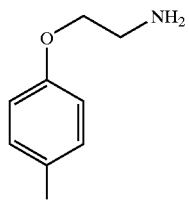

PIB
(avg. molecular weight ~950)

Dehydrated 4-polyisobutyl phenol solution like prepared in Example 1 (400.0 grams) and 1-decanol (45.3 grams, 98.5% assay from Aldrich), were added to a separate 1-L reactor equipped with a total reflux condenser and nitrogen purge. The reaction mixture was heated to about 150° C. at atmospheric pressure under nitrogen purge. After adding 2-oxazolidinone (25.1 grams, assay 99%, from Avocado Research Chemicals Ltd.) to the reactor at 150° C., the temperature was increased to about 180° C. Nitrogen purging was stopped and the pressure was lowered to about 720 mm Hg in order to cause steady refluxing. The temperature was held at about 180° C. for four hours and the pressure adjusted to about 730 mm Hg to maintain vigorous refluxing. This pressure was higher than in Comparative Examples B and C suggesting the formation of an azeotrope with the aromatic solvent and possibly dehydration of the alcohol at theses conditions.

The reactor was cooled to about 85° C. and a yielded 448.4 grams of crude product. After removing a sample, magnesium silicate (11.7 grams Magnesol HMR LS), filter aid (1.17 grams of Celite HyFlo Super Cel), and deionized water (2.06 grams) were added to the remaining 421.7 grams of crude product and the mixture stirred for one hour at about 85° C. The crude product mixture was filtered with a pressure filter and yielded 392.9 grams of amber colored filtrate and 33 grams of filter cake. Table 2 summarizes the properties of the filtrate.

This example shows that there is no benefit, and in fact a detriment, to using 1-decanol compared to none in Comparative Example A. Conversion of 4-polyisobutyl phenol (Table 2) was only 51% compared to 71% in Comparative Example A. The filtrate color was also much darker than any other filtrate listed in Table 2. This example again confirms that alcohol molecular weight is an important consideration and that lower than C8 alcohols (straight-chain or branched) are preferred.

Comparative Example E

No Alcohol, No Alkylation Catalyst Sediment

Preparation of Solution Containing

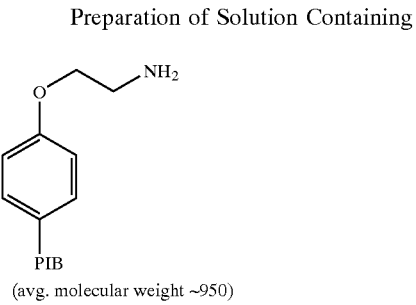

PIB
(avg. molecular weight ~950)

Dehydrated 4-polyisobutyl phenol solution from Example 3 (353.0 grams) and ExxonMobil Aromatic 100 Solvent (47.0 grams) were added to a separate 1-L reactor equipped with a total reflux condenser and nitrogen purge. The reaction mixture was heated to about 150° C. at atmospheric pressure under nitrogen purge. After adding 2-oxazolidinone (23.7 grams, assay 99%, from Avocado Research Chemicals Ltd.) to the reactor at 150° C., the temperature was increased to about 180° C. Nitrogen purging was stopped and the pressure was lowered to about 730 mm Hg in order to cause steady refluxing. The temperature was held at about 180° C. for four hours and the pressure adjusted gradually to about 690 mm Hg to maintain vigorous refluxing.

The reactor was cooled to about 85° C. and a yielded 412.3 grams of crude product. After removing a sample, magnesium silicate (6.32 grams Magnesol HMR LS), filter aid (0.67 grams of Celite HyFlo Super Cel), and deionized water (2.06 grams) were added to the remaining 386 grams of crude product and the mixture stirred for one hour at about 85° C. The crude product mixture was filtered with a pressure filter and yielded 366.4 grams of amber colored filtrate and 18.3 grams of filter cake. Table 2 summarizes the properties of the filtrate.

The aminoethylate content of the polymer was 66%. The conversion of 4-polyisobutyl phenol was 76% and the selectivity to aminoethylate was 91% (Table 2). The color was very light at L 2.0 (ASTM D1500) compared to Comparative Example A. The nitrogen content of the filtrate indicated that about 87% of the 2-oxazolidinone was utilized in the product.

Comparison of the results of this example with Comparative Example A shows that leaving the sediment from the neutralized alkylation catalyst in the solution of 4-polyisobutyl phenol has a detrimental effect on 4-polyisobutyl phenol conversion, aminoethylate content of the polymer, and light color. Examples 1–2 show how the hexanol mitigates the negative effects of the sediment in the 4-polyisobutyl phenol of Comparative Example A.

Comparative Example F

No Improvement Using 2-Ethylhexanol

Preparation of Solution Containing

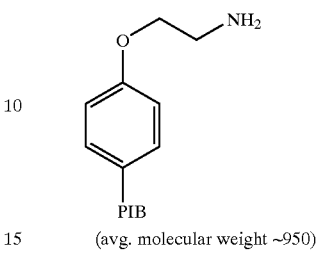

PIB
(avg. molecular weight ~950)

Dehydrated 4-polyisobutyl phenol solution from Example 3 (400.0 grams) and 2-ethyl-1-hexanol (39.8 grams, 99.8% assay from Aldrich), were added to a separate 1-L reactor equipped with a total reflux condenser and nitrogen purge. The reaction mixture was heated to about 150° C. at atmospheric pressure under nitrogen purge. After adding 2-oxazolidinone (26.8 grams, assay 99%, from Avocado Research Chemicals Ltd.) to the reactor at 150° C., the temperature was increased to about 180° C. Nitrogen purging was stopped and the pressure was lowered to about 740 mm Hg in order to cause reflux. The temperature was held at 180° C. for four hours and the pressure gradually lowered to 662 mm Hg to maintain vigorous refluxing.

The reactor was cooled to about 85° C. and a yielded 449.4 grams of crude product. After removing a sample, magnesium silicate (7.16 grams Magnesol HMR LS), filter aid (0.72 grams of Celite HyFlo Super Cel), and deionized water (2.27 grams) were added to the remaining 422.3 grams of crude product and the mixture stirred for one hour at about 85° C. The crude product mixture was filtered with a pressure filter and yielded 399 grams of amber colored filtrate and 18.1 grams of filter cake. Table 3 summarizes the properties of the filtrate.

This example shows that the use of 2-ethyl-1-hexanol was detrimental to 4-polyisobutyl phenol conversion and aminoethylate content in the polymer compared to Comparative Example E when no alcohol was used. The filtrate color was also very dark compared to the filtrate in Comparative Example E and Example 3.

Table 1 summarizes the key variables covered in the examples while Table 2 summarizes the results.

TABLE 1

Summary of Key Variables in Examples

| Example | Condition of Starting 4-Polyisobutylphenol Solution* | Alcohol |
|---|---|---|
| 1 | Unfiltered | 1-Hexanol |
| 2 | Unfiltered | Hexanol, Mixed Isomer |
| 3 | Filtered | 1-Hexanol |
| Comparative A | Unfiltered | None |
| Comparative B | Unfiltered | 1-Octanol |
| Comparative C | Unfiltered | 2-Ethylhexanol |
| Comparative D | Unfiltered | 1-Decanol |
| Comparative E | Filtered | None |
| Comparative F | Filtered | 2-Ethylhexanol |

*Unfiltered solution contains sediment from neutralized $BF_3$ alkylation catalyst.

TABLE 2

Summary of Results

| | Examples | | | Comparative Examples | | | | | |
|---|---|---|---|---|---|---|---|---|---|
| | 1 | 2 | 3 | A | B | C | D | E | F |
| Alkylphenol Conversion, % | 85 | 84 | 81 | 71 | 76 | 73 | 51 | 76 | 67 |
| Selectivity to Aminoethylate, % | 90 | 89 | 87 | 91 | 92 | 92 | 63 | 91 | 80 |
| Filtrate Properties | | | | | | | | | |
| Polymer Content, % | 67.1 | 67.1 | 72.8 | 69.6 | 65.6 | 65.5 | 66.3 | 69.1 | 72.3 |
| Aminoethylate in Polymer, % | 72 | 71 | 68 | 62 | 67 | 65 | 31 | 66 | 51 |
| Basic N in Polymer, % | 1.02 | 1.03 | 1.01 | 0.892 | 0.947 | 0.925 | 0.538 | 0.955 | 0.790 |
| Total N in Polymer, % | 1.27 | 1.27 | 1.25 | 1.20 | 1.23 | 1.22 | 0.957 | 1.18 | 1.15 |
| N Uptake from 2-Ox., % | 91 | 90 | 92 | 87 | 88 | 88 | 68 | 87 | 86 |
| Filtrate Color, D1500 | L3.0 | 2.5 | L2.0 | 5.5 | 6.5 | 5.0 | *4.5D | L2.0 | 6.5 |

*Diluted 15 volumes of sample to 85 volumes of solvent.

What is claimed is:

1. A process for the preparation of a polyalkylphenoxyaminoalkane which comprises the aminoethylation of a polyalkylphenol compound in the presence of a basic catalyst with 2-oxazolidinone or a derivative thereof having the following formula:

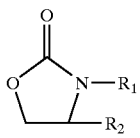

wherein $R_1$ and $R_2$ are independently hydrogen or lower alkyl having 1 to about 6 carbon atoms and wherein the polyalkyl group of said polyalkylphenol has an average molecular weight in the range of about 600 to 5,000 and wherein the process is carried out in the presence of an alcohol having the following formula:

wherein $R_3$ is an alkyl group having from about 3 to 7 carbon atoms.

2. The process according to claim 1, wherein the polyalkyl group has a molecular weight in the range of about 600 to 3,000.

3. The process according to claim 2, wherein the polyalkyl group has a molecular weight in the range of about 700 to 3,000.

4. The process according to claim 3, wherein the polyalkyl group has a molecular weight in the range of about 900 to 2,500.

5. The process according to claim 4, wherein the polyalkyl group is derived from polypropylene, polybutene, or a polyalphaolefin oligomer of 1-octene or 1-decene.

6. The process according to claim 5, wherein the polyalkyl group is derived from polyisobutene.

7. The process according to claim 6, wherein the polyisobutene contains at least about 20 wt % of a methylvinylidene isomer.

8. The process according to claim 1, wherein one of $R_1$ and $R_2$ is hydrogen or lower alkyl of 1 to about 4 carbon atoms, and the other is hydrogen.

9. The process according to claim 8, wherein one of $R_1$ and $R_2$ is hydrogen, methyl, or ethyl, and the other is hydrogen.

10. The process according to claim 9, wherein $R_1$ is hydrogen, methyl, or ethyl and $R_2$ is hydrogen.

11. The process according to claim 10, wherein both $R_1$ and $R_2$ are hydrogen.

12. The process according to claim 1, wherein the basic catalyst is selected from the group consisting of alkali metal lower alkoxide, alkali hydride or alkali metal hydroxide.

13. The process according to claim 12, wherein the alkali metal lower alkoxide is selected from the group consisting of sodium methoxide, potassium methoxide, sodium ethoxide, potassium ethoxide, sodium propoxide, potassium propoxide, sodium isopropoxide, potassium isopropoxide, sodium butoxide, potassium butoxide.

14. The process according to claim 13, wherein the alkali metal lower alkoxide is sodium methoxide.

15. The process according to claim 12, wherein the alkali hydride is sodium hydride or potassium hydride.

16. The process according to claim 12, wherein the alkali metal hydroxide is selected from the group consisting of sodium hydroxide, lithium hydroxide, or potassium hydroxide.

17. The process according to claim 16, wherein the alkali metal hydroxide is sodium hydroxide or potassium hydroxide.

18. The process according to claim 1, wherein the aminoethylation temperature is in the range of about 100° C. to 250° C.

19. The process according to claim 18, wherein the aminoethylation temperature is in the range of about 130° C. to 210° C.

20. The process according to claim 1, wherein the molar ratio of 2-oxazolidinone or a derivative thereof to polyalkylphenol compound is about 5:1 to 0.9:1.

21. The process according to claim 20, wherein the molar ratio of 2-oxazolidinone or a derivative thereof to polyalkylphenol compound is about 2:1 to 1:1.

22. The process according to claim 1, wherein the number of equivalents of basic catalyst per equivalent of polyalkylphenol is about 0.05:1 to 1:1.

23. The process according to claim 22, wherein the number of equivalents of basic catalyst per-equivalent of polyalkylphenol is about 0.1:1 to 1:1.

24. The process according to claim 1, wherein $R_3$ is an alkyl group having about 5 to 7 carbon atoms.

25. The process according to claim 24, wherein $R_3$ is an alkyl group having about 6 carbon atoms.

26. The process according to claim 25, wherein the alcohol is hexanol, either branched, straight chain or mixtures thereof.

27. The process according to claim 1, wherein the molar ratio of alcohol to polyisobutylphenol is about 0.2:1 to 5:1.

28. The process according to claim 27, wherein the molar ratio of alcohol to polyisobutylphenol is about 0.4:1 to 2:1.

29. The process according to claim 28, wherein the molar ratio of alcohol to polyisobutylphenol is about 0.5:1 to 1.5:1.

* * * * *